United States Patent
Miller et al.

(10) Patent No.: US 6,221,022 B1
(45) Date of Patent: Apr. 24, 2001

(54) MULTIPLE TRANSMIT SCANNING TO INCREASE ULTRASONIC FRAME RATE

(75) Inventors: Steven Charles Miller, Waukesha; David Thomas Dubberstein, Hales Corners, both of WI (US)

(73) Assignee: G.E. Medical Systems Global Technology Company LLC, Waukesha, WI (US)

(*) Notice: Subject to any disclaimer, the term of this patent is extended or adjusted under 35 U.S.C. 154(b) by 0 days.

(21) Appl. No.: 09/542,057

(22) Filed: Apr. 3, 2000

(51) Int. Cl.[7] .................................................. A61B 8/00

(52) U.S. Cl. ......................................... 600/459; 600/447

(58) Field of Search .................................... 600/459, 455, 600/456, 457, 458, 443, 447, 449

(56) References Cited

U.S. PATENT DOCUMENTS

| 5,301,674 | 4/1994 | Erikson et al. . |
| 5,865,750 | 2/1999 | Hatfield et al. . |
| 5,908,391 | * 6/1999 | Muzilla et al. ...................... 600/454 |
| 5,911,692 | * 6/1999 | Hussain et al. ...................... 600/447 |
| 6,048,313 | * 4/2000 | Stonger ................................ 600/443 |

* cited by examiner

Primary Examiner—Marvin M. Lateef
Assistant Examiner—Maulin Patel
(74) Attorney, Agent, or Firm—McAndrews, Held & Malloy, Ltd.

(57) ABSTRACT

A transducer (10) is controlled by a beam former (20) to transmit ultrasound pulses in multiple transmit focal zones (Z1–Z3) along at least two axes (A1 and A2). The beam former (20) causes the transducer (10) to transmit a first transmit pulse along one axis (A1) and to transmit a second transmit pulse along another axis (A2) before the echo pulse from the first transmit pulse is received by the transducer in order to decrease frame rates.

18 Claims, 2 Drawing Sheets

MULTIPLE TRANSMIT SCANNING TO INCREASE ULTRASONIC FRAME RATE

BACKGROUND OF THE INVENTION

Some commercial ultrasound scanners use multiple transmit focal zones. One example of such a scanner is the General Electric Logiq 700. However, there is a disadvantage of using the multiple transmit focal zones, namely, changing the focal number affects the frame rate. The greater the number of focal zones, the slower the frame rate.

One proposal for increasing frame rate is described in U.S. Pat. No. 5, 301,674 (Erikson et al., issued Apr. 12, 1994, the "'674 Patent"). FIG. 2E illustrates a method in which the various focal zones are subjected to ultrasound transmit pulses one at a time in increasing distance from the source of the pulses. A guard time is used between each ultrasound pulse, and the timing is such that the echo pulse responsive to each transmitted pulse is received before the next transmit pulse is generated.

The '674 Patent approach does not increase frame rate to the extent needed in modem ultrasound scanners. This invention addresses the problem and provides a solution.

BRIEF SUMMARY OF THE INVENTION

The preferred embodiment is useful in an ultrasound scanner for transmitting ultrasound transmit pulses in multiple transmit focal zones within a subject being studied. In such an environment, the preferred embodiment improves the frame rate of the transmit pulses by transmitting a first ultrasound beam of the transmit pulses along a first axis and transmitting a second ultrasound beam of the transmit pulses along a second axis displaced from the first axis by a predetermined distance, preferably with an ultrasound transducer. Echo pulses are received from the subject in response to the transmit pulses. The transducer is caused to transmit a first one of the transmit pulses along the first axis and to transmit a second one of said transmit pulses along the second axis before the echo pulse from said first transmit pulse is received by the transducer. The transducer preferably is controlled by a beam former.

According to another aspect of the invention, the focal zones are arrange in a predetermined order with respect to the transducer, and the transmit pulses are transmitted to the focal zones in an order different than the predetermined order.

By using the foregoing techniques, the frame rate of a multiple transmit focal zone ultrasound scanner can be increased to a substantial extent.

DETAILED DESCRIPTION OF THE INVENTION

Figure 1:
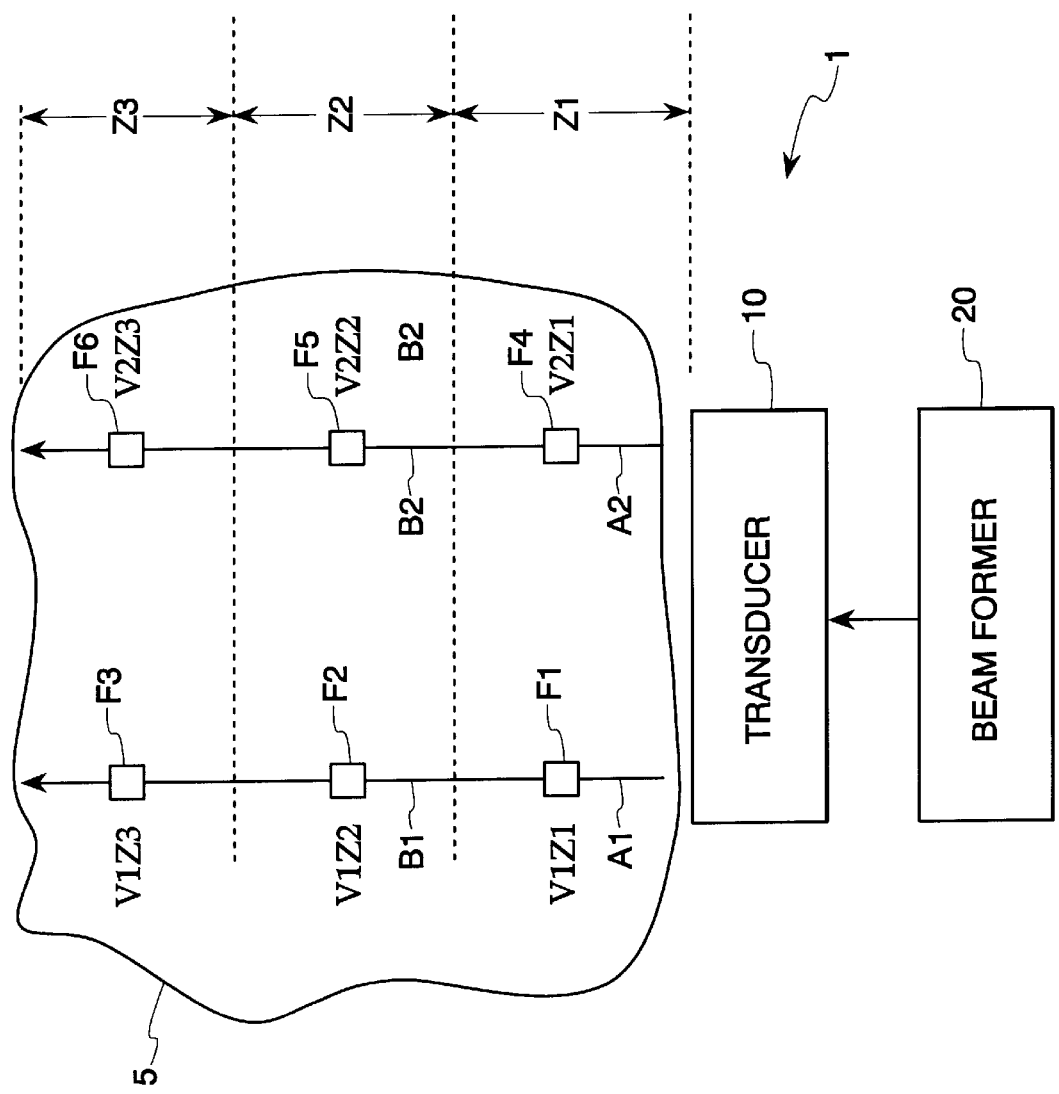
FIG. 1 is a schematic block diagram of a preferred form of apparatus made in accordance with the present invention and a vector diagram illustrating a preferred arrangement of ultrasound beam axes and focal zones in accordance with the invention.

Referring to FIG. 1, an ultrasound scanner 1 according to the preferred embodiment includes an ultrasound transducer 10 which is operated by a beam former in order to generate ultrasound beams B1 and B2 of ultrasound transmit pulses along parallel axes A1 and A2. The transmit pulses are focused at multiple focal nodes F1–F6 as shown. The focal nodes are located in zones Z1–Z3 as shown. Axes A1 and A2 are separated by the length of a focal transmit zone, such as the length of zone Z1. Zones Z1–Z3 are arranged to lie within a subject under study S.

Ultrasound transducers and beam formers capable of creating multiple transmit focal zones are well known in the art. For example, such a transducer and beam former is described in U.S. Pat. No. 5,865,750 (Hatfield et al., issued Feb. 2, 1999) which is assigned to a parent of the assignee of this application and which is incorporated by reference.

According to the preferred embodiment, a multiple transmit scan is used to increase the frame rate by producing multiple transmit beams in the time a conventional scanner produces a single transmit beam. The multiple transmit beams propagate from transducer 10 separated by only the length of a transmit focal zone, such as the length of zone Z1. The transducer excitation sequences are timed such that the transmit beams produced are both axially and laterally separated. The axial direction is shown in FIG. 1 by AX and the lateral direction is shown by LA. The beam scan uses only one parallel receive line (not shown) to achieve the increases in frame rate.

In a three focal zone scan, the transmit focal zones Z1–Z3 are distributed in the ranges shown in FIG. 1. The transmit vector locations of the transmit pulses are denoted with a matrix convention. For example, the transmit focal zone labeled V2Z3 stands for vector 2 which extends along axis A2, and Z3 which denotes transmit focal zone Z3. For this example, the transmit zone nearest transducer 10, zone Z1, would take a conventional scanner 50 $\mu$seconds to obtain, the middle zone, Z2, would take 100 $\mu$seconds to obtain, and the farthest zone, Z3, would take 150 $\mu$seconds to obtain.

The excitation sequence for the preferred form of scan starts with the generation of a first transmit pulse for the farthest transmit zone, zone Z3, for vector V2 (along axis A2), labeled V2Z3. Then, 50 $\mu$seconds later a second transmit pulse is generated for the nearest transmit zone, Zone 1, for vector V1 (along axis A1), labeled V1Z1. The receive echo pulse signals for both focal zones Z3 and Z1 then are acquired over the next 100 $\mu$seconds. The process is repeated with the transmit sequence excitation for the farthest transmit zone, zone Z3, for vector V1 (along axis A1), labeled as V1Z3. Then, 50 $\mu$seconds later, a second transmit pulse is generated for the nearest transmit zone, zone Z1, for vector V2 (along axis A2), labeled V2Z1. The receive echo pulse signals for both focal zones then are acquired over the next 100 $\mu$seconds. To finish the data acquisition for vectors V1 and V2, the middle transmit zone, zone Z2, for vectors V1 and V2 (along axes A1 and A2, respectively), labeled V1Z2 and V2Z2 of FIG. 1, are acquired using conventional transmission. As illustrated in FIG. 1, the focal zones are arrange in a predetermined order, Z1–Z3, with respect to transducer 10. The transmit pulses are transmitted to the focal zones in a different order Z3, Z1, Z2.

Figure 2:
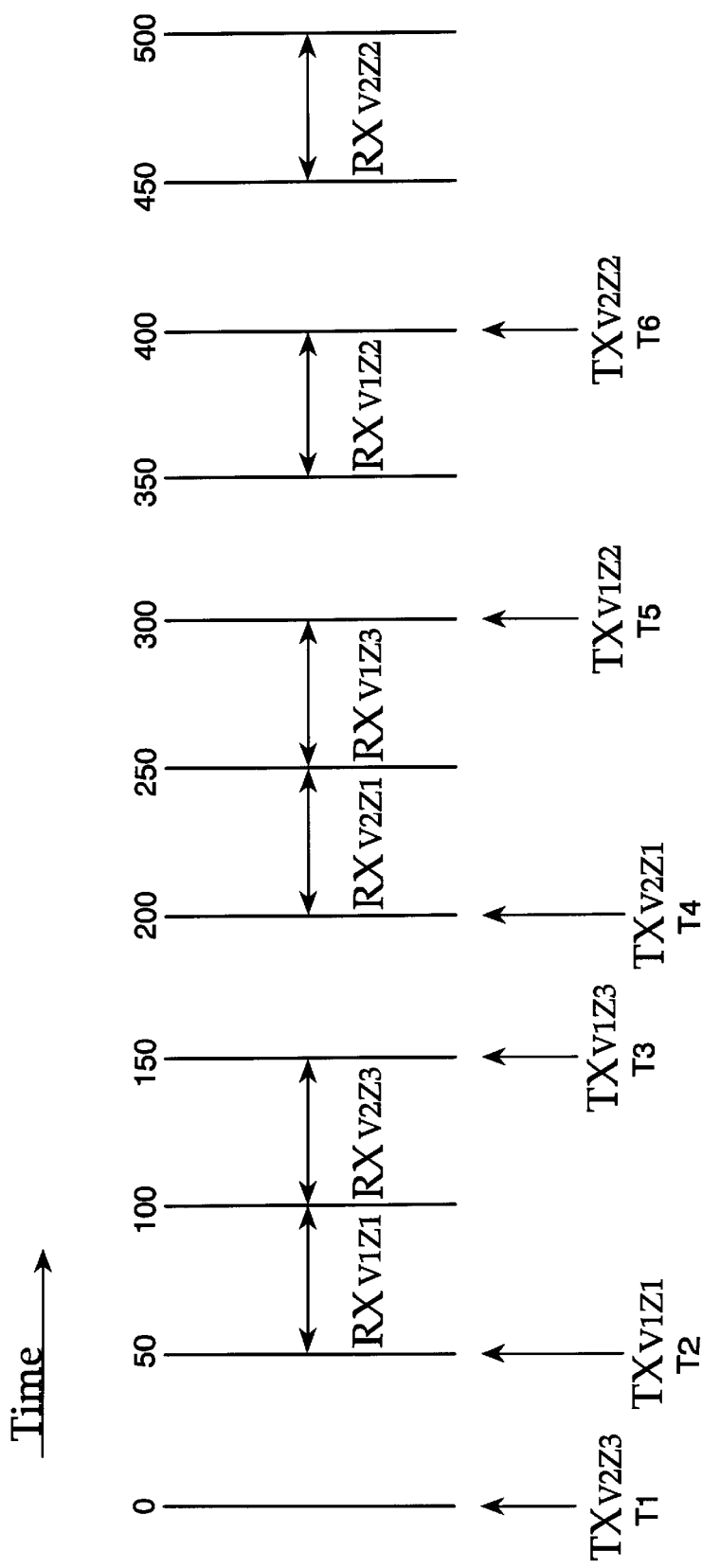
FIG. 2 is a vector timing diagram illustrating a preferred form of timing of ultrasound transmit pulses in accordance with the invention in which the horizontal axis represents time in units of $\mu$seconds.

The timing diagram for the embodiment of FIG. 1 is shown in FIG. 2. For the example of FIG. 2, the preferred embodiment requires 500 $\mu$seconds to acquire two, three focal zone vectors. Zone Z1 is located at a first range of distances from transducer 10 such that echo pulses from zone Z1 are expected to be received at transducer 10 within 0–50 $\mu$seconds. Zone Z2 is located at a second range of distances from transducer 10 such that echo pulses from zone Z2 are expected to be received at transducer 10 within 50–100 μseconds. Zone Z3 is located at a third range of distances from transducer 10 such that echo pulses from zone Z3 are expected to be received at transducer 10 within 100–150 μseconds.

Beam former 20 causes transducer 10 to transmit a first transmit pulse along axis A2 at a time T1 such that a first echo pulse responsive to said first transmit pulse is expected at transducer 10 from zone Z3 along axis A2 within 100–150 μseconds after time T1. Beam former 20 then causes transducer 10 to transmit a second transmit pulse along axis A1 at time T2 such that a second echo pulse responsive to said second transmit pulse is expected at transducer 10 from zone Z1 along axis A1 during the time period 0–50 μseconds after time T2, before the first echo pulse is expected at transducer 10 from zone Z3 along axis A2 during the time period 100–150 μseconds after time T1.

The foregoing procedure is repeated at times T3 and T4 for additional transmit pulses sent along axes A1 and A2, respectively as shown in FIG. 2.

Specifically, beam former 20 causes transducer 10 to transmit a third transmit pulse along the axis A1 at time T3 occurring at or later than the 100–150 μsecond time period after time T1 such that a third echo pulse responsive to said third transmit pulse is expected at transducer 10 from zone Z3 along axis A1 during a time period100–150 μseconds after time T3.

Beam former 20 causes transducer 10 to transmit a fourth transmit pulse along axis A2 at time T4 such that a fourth echo pulse is expected at transducer 10 from zone Z1 along axis A2 before the third echo pulse is expected at transducer 10 from zone Z3 along axis A1.

Beam former 20 causes transducer 10 to transmit a fifth transmit pulse along axis A1 at time T5 such that a fifth echo pulse is expected at transducer 10 from zone Z2 along axis A1 within a 50–100 μsecond time period after time T5.

Beam former 20 causes transducer 10 to transmit a sixth transmit pulse along axis A2 at time T6 occurring at or after the end of the 50–100 μsecond time period occurring after time T5 such that a sixth echo pulse is expected at transducer 10 from zone Z2 along axis A2 within a 50–100 μsecond time period occurring after time T6.

As shown in FIG. 2, the time period between T1 and T2 and the time period between T3 and T4 is less than the time period between times T2 and T3 and between times T4 and T5.

Those skilled in the art will recognize that the preferred embodiments can be altered and modified without departing from the true spirit and scope of the invention as defined in the accompanying claims.

What is claimed is:

1. In an ultrasound scanner for transmitting ultrasound transmit pulses in multiple transmit focal zones within a subject being studied, apparatus for improving the frame rate of the transmit pulses comprising:

a transducer arranged to transmit a first ultrasound beam of said transmit pulses along a first axis and to transmit a second ultrasound beam of said transmit pulses along a second axis displaced from the first axis by a predetermined distance and to receive echo pulses from the subject in response to the transmit pulses;

a beam former arranged to cause said transducer to transmit a first one of said transmit pulses along the first axis and to transmit a second one of said transmit pulses along the second axis before the echo pulse from said first transmit pulse is received by said transducer.

2. Apparatus, as claimed in claim 1, wherein the focal zones are arrange in a predetermined order with respect to said transducer, and wherein the transmit pulses are transmitted to said focal zones in an order different than the predetermined order.

3. Apparatus, as claimed in claim 1, wherein said focal zones comprise a first zone located at a first range of distances from said transducer such that echo pulses from the first range are expected to be received at the transducer within a first time period, a second zone located at a second range of distances from said transducer such that echo pulses from the second range are expected to be received at the transducer within a second time period and a third zone located at a third range of distances from said transducer such that echo pulses from the third range are expected to be received at the transducer within a third time period, said second range of distances being located farther from said transducer than said first range of distances, and said third range of distances being located farther from said transducer than said second range of distances such that said second time period occurs after said first time period, and said third time period occurs after said second time period.

4. Apparatus, as claimed in claim 3, wherein said beam former causes said transducer to transmit said first transmit pulse along the first axis at a first time such that a first echo pulse responsive to said first transmit pulse is expected at said transducer from said third zone along said first axis during said third time period and wherein said beam former causes said transducer to transmit said second transmit pulse along said second axis at a second time such that a second echo pulse responsive to said second transmit pulse is expected at said transducer from said first zone along said second axis during said first time period before said first echo pulse is expected at said transducer from said third zone along said first axis during said third time period.

5. Apparatus, as claimed in claim 4, wherein said beam former causes said transducer to transmit a third transmit pulse along the second axis at a third time occurring at or later than said third time period such that a third echo pulse responsive to said third transmit pulse is expected at said transducer from said third zone along said second axis during said third time period.

6. Apparatus, as claimed in claim 5, wherein said beam former causes said transducer to transmit a fourth transmit pulse along said first axis at a fourth time such that a fourth echo pulse is expected at said transducer from said first zone along said first axis before said third echo pulse is expected at said transducer from said third zone along said first axis.

7. Apparatus, as claimed in claim 6, wherein said beam former causes said transducer to transmit a fifth transmit pulse along said second axis at a fifth time such that a fifth echo pulse is expected at said transducer from said second zone along said second axis within said second time period.

8. Apparatus, as claimed in claim 7, wherein said beam former causes said transducer to transmit a sixth transmit pulse along said first axis at a sixth time occurring at or after the end of the second time period triggered by the fifth transmit pulse such that a sixth echo pulse is expected at said transducer from said second zone along said first axis within said second time period.

9. Apparatus, as claimed in claim 8, wherein the time period between said first and second times and the time period between said third and fourth times is less than the time period between said second and third times and the time period between said fourth and fifth times.

10. In an ultrasound scanner for transmitting ultrasound transmit pulses in multiple transmit focal zones within a subject being studied by means of a transducer, a method of improving the frame rate of the transmit pulses comprising:

transmitting a first ultrasound beam of said transmit pulses along a first axis;

transmit a second ultrasound beam of said transmit pulses along a second axis displaced from the first axis by a predetermined distance;

receiving echo pulses from the subject in response to the transmit pulses;

causing said transducer to transmit a first one of said transmit pulses along the first axis and to transmit a second one of said transmit pulses along the second axis before the echo pulse from said first transmit pulse is received by said transducer.

11. A method, as claimed in claim 10, wherein the focal zones are arrange in a predetermined order with respect to said transducer, and wherein the transmit pulses are transmitted to said focal zones in an order different than the predetermined order.

12. A method, as claimed in claim 10, wherein said focal zones comprise a first zone located at a first range of distances from said transducer such that echo pulses from the first range are expected to be received at the transducer within a first time period, a second zone located at a second range of distances from said transducer such that echo pulses from the second range are expected to be received at the transducer within a second time period and a third zone located at a third range of distances from said transducer such that echo pulses from the third range are expected to be received at the transducer within a third time period, said second range of distances being located farther from said transducer than said first range of distances, and said third range of distances being located farther from said transducer than said second range of distances such that said second time period occurs after said first time period, and said third time period occurs after said second time period.

13. A method, as claimed in claim 12, wherein said causing said transducer to transmit comprises causing said transducer to transmit said first transmit pulse along the first axis at a first time such that a first echo pulse responsive to said first transmit pulse is expected at said transducer from said third zone along said first axis during said third time period and causing said transducer to transmit said second transmit pulse along said second axis at a second time such that a second echo pulse responsive to said second transmit pulse is expected at said transducer from said first zone along said second axis during said first time period before said first echo pulse is expected at said transducer from said third zone along said first axis during said third time period.

14. A method, as claimed in claim 13, wherein said causing said transducer to transmit comprises causing said transducer to transmit a third transmit pulse along the second axis at a third time occurring at or later than said third time period such that a third echo pulse responsive to said third transmit pulse is expected at said transducer from said third zone along said second axis during said third time period.

15. A method, as claimed in claim 14, wherein said causing said transducer to transmit comprises causing said transducer to transmit a fourth transmit pulse along said first axis at a fourth time such that a fourth echo pulse is expected at said transducer from said first zone along said first axis before said third echo pulse is expected at said transducer from said third zone along said first axis.

16. A method, as claimed in claim 15, wherein said causing said transducer to transmit comprises causing said transducer to transmit a fifth transmit pulse along said second axis at a fifth time such that a fifth echo pulse is expected at said transducer from said second zone along said second axis within said second time period.

17. A method, as claimed in claim 16, wherein said causing said transducer to transmit comprises causing said transducer to transmit a sixth transmit pulse along said first axis at a sixth time occurring at or after the end of the second time period triggered by the fifth transmit pulse such that a sixth echo pulse is expected at said transducer from said second zone along said first axis within said second time period.

18. A method, as claimed in claim 17, wherein the time period between said first and second times and the time period between said third and fourth times is less than the time period between said second and third times and the time period between said fourth and fifth times.

\* \* \* \* \*